United States Patent [19]
Aaslyng et al.

[11] Patent Number: 5,985,629
[45] Date of Patent: Nov. 16, 1999

[54] CLEANING AND DISINFECTING CONTACT LENSES WITH A PROTEASE AND CHLORAMINE-T OR CHLORAMINE-B

[75] Inventors: Dorrit Aaslyng, Værløse; Jack Bech Nielsen, Hellerup; Lone Kierstein Nielsen, Lyngby, all of Denmark

[73] Assignee: Novo Nordisk A/S, Bagsvaerd, Denmark

[21] Appl. No.: 08/776,934

[22] PCT Filed: Sep. 11, 1995

[86] PCT No.: PCT/DK95/00363

§ 371 Date: Feb. 12, 1997

§ 102(e) Date: Feb. 12, 1997

[87] PCT Pub. No.: WO96/07324

PCT Pub. Date: Mar. 14, 1996

[30] Foreign Application Priority Data

Sep. 9, 1994 [DK] Denmark .................. 1037/94

[51] Int. Cl.⁶ .............. C12N 11/00; C12N 9/50; A61K 38/48; C06M 16/00
[52] U.S. Cl. ............. 435/174; 424/94.63; 424/94.64; 424/464; 435/177; 435/178; 435/182; 435/219; 435/262; 435/264
[58] Field of Search .................... 435/262, 264, 435/267, 268, 269, 174, 177, 178, 182, 219; 424/94.63, 94.64, 94.67, 464

[56] References Cited

U.S. PATENT DOCUMENTS

| | | | |
|---|---|---|---|
| 3,910,296 | 10/1975 | Karageozian et al. | 134/2 |
| 4,155,868 | 5/1979 | Kaplan et al. | 252/95 |
| 4,670,178 | 6/1987 | Huth et al. | 252/95 |

FOREIGN PATENT DOCUMENTS

| | | |
|---|---|---|
| 1146881 | 5/1983 | Canada . |
| 2044072 | 12/1992 | Canada . |
| 0196151 | 10/1986 | European Pat. Off. . |
| 0257942 | 3/1988 | European Pat. Off. . |
| 0279401 | 8/1988 | European Pat. Off. . |
| WO 9317720 | 9/1993 | WIPO . |

OTHER PUBLICATIONS

STN International, CAPLUS accession No. 1992: 158988.

Powers, et. al., Res. Monogr. Cell Tissue Physiol. 12:55–152, 1986.

*Primary Examiner*—David M. Naff
*Attorney, Agent, or Firm*—Steve T. Zelson, Esq.; Reza Green, Esq.

[57] ABSTRACT

Contact lens are cleaned and disinfected by contacting with an enzyme that functions as a cleaning agent by degrading deposits on the lens, and with an enzyme inhibitor that inhibits remaining enzyme activity and a mild disinfecting agent. If rinsing of the lens is not carried out after cleaning and disinfecting, this procedure prevents eye damage by inhibiting remaining enzyme activity and using a mild disinfectant. Preferred enzymes are proteases such as an acidic aspartic protease, a cysteine protease, a serine protease or a metalloprotease, and preferred enzyme inhibitors function both as an inhibitor and as a mild disinfectant such as chloramine-T, chloramine-B, bacitracin or aryl boronic acids. In a preferred method, the enzyme is subtilisin A and the enzyme inhibitor and disinfectant is chloramine-T. The method may be carried out with a solution containing the enzyme and a tablet containing the enzyme inhibitor and disinfectant or with two tablets where one contains the enzyme and the other contains the enzyme inhibitor and disinfectant or with a multi-layer tablet where an outer layer contains the enzyme and an inner layer contains the enzyme inhibitor and disinfectant. The inner and outer layers may be separated by a barrier layer made of a water soluble polymer. A controlled release tablet is preferred.

21 Claims, No Drawings

CLEANING AND DISINFECTING CONTACT LENSES WITH A PROTEASE AND CHLORAMINE-T OR CHLORAMINE-B

CROSS-REFERENCE TO RELATED APPLICATIONS

This application is a 35 U.S.C. 371 national application of PCT/DK95/00363 filed Sep. 11, 1995 and claims priority under 35 U.S.C. 119 of Danish application 1037/94 filed Sep. 9, 1994, the contents of which are fully incorporated herein by reference.

FIELD OF THE INVENTION

The present invention relates to a method of cleaning, disinfecting and preserving contact lenses, a contact lens cleaning, disinfecting and preserving product, a tablet or capsule for cleaning, disinfecting and preserving contact lenses and the use of an enzyme inhibitor for cleaning, disinfecting and preserving contact lenses.

BACKGROUND OF THE INVENTION

To enjoy the advantages gained by wearing contact lenses it is necessary to carry out the time consuming and cumbersome task of cleaning and disinfection the contact lenses. The procedure differs depending on the type of contact lenses in question e.g. hard lenses or soft lenses.

In all cases, the contact lenses need to be cleaned and disinfected periodically, to avoid infection and discomfort for the wearer, in some cases every morning or evening.

When removed from the eyes the lenses must be stored in a preserving solution. Before wearing the lenses again they must be cleaned, disinfected and rinsed.

The cleaning operation is carried out to remove deposits and debris from the surface of the contact lenses. The cleaning effect is often obtained by treatment with enzymes such as proteases, capable of hydrolysing proteinaceous material to smaller water-soluble subunits.

Disinfection of the contact lenses prevents growth of bacteria on the contact lenses which might lead to infection of the eyes and making it impossible to wear contact lenses for a long period of time. Disinfecting agents such as hydrogen peroxide is widely used.

After the cleaning and/or disinfecting procedure the contact lenses need to be rinsed, to make sure that all enzymatic activities and/or disinfecting agent are removed, e.g. by using a physiological saline solution.

When the contact lenses are not worn the lenses need to be stored under sanitary conditions to secure that they are ready in a clean state for the next wear.

Further it is also important to make sure that the lenses are treated with care to secure that e.g. the shape of the contact lenses is maintained, staining of the lenses is prevented, an acceptable oxygen permeability of the lenses is maintained etc.

Soil deposits are found on all groups of contact lenses, but the easiness of removal differs among the groups. Hard contact lenses are easy to clean, due to only small amounts of soil deposited, and ease of removing soil by rubbing. Soft hydrophillic lenses are more prone to adsorption of soil which is difficult to remove. One reason is that hard rubbing and abrasives might damage the lens.

The major important soil deposits on contact lenses are proteins, lipid deposits and Jelly bumps, mucins, pigments and inorganic compounds.

Wedler (J. Biomed. Mater. Res. Vol. 11, p. 525–535, 1977) has identified tear proteins from extracts of contact lenses. Per lens was found 5–10 $\mu$g protein, 1.0–1.2 $\mu$g carbohydrates, 5–25 $\mu$g phospholipids. Cholesterol and glucose were not detected. Albumin, lysozyme, IgG and $\alpha_1$-lipoprotein were found in the deposits.

The main component of Jelly bumps deposits are lipids (Bilbaut et al., Exp. Eys. Res., Vol. 43, p. 153–165, 1986). These are often seen on contact lenses with high water content, particularly extended wear contact lenses (Pohlzhofer, Deutsche Optiker Zeitung, Vol. 40, p.40–100, 1985 and Sack et al. Investigative Ophthalmology & Visual Science, Vol. 28, p. 842–849, 1987).

A plethora of methods for removing deposits from contact lenses are known. Contact lenses are often cleaned with enzymes. U.S. Pat. No. 3,910,296 (Allergan) describes a method for cleaning contact lenses by the use of a protease.

U.S. Pat. No. 4,670,178 (Allergan) discloses a method for simultaneous cleaning and disinfection contact lenses with a protease in hydrogen peroxide. The cleaning is effected by protease and shown to be very efficient.

CA 1,146,881 (Bedding) points out a method for cleaning contact lenses using enzymes, where the cleaning procedure is followed by rinsing of the lenses, e.g. with saline, to remove active enzymes from the lens.

EP patent nr. 257.942 (Hoya Corporation) describes a contact lens cleaning kit comprising an oxidising agent and reducing agent in such a form that they do not react with each other in the kit. When placed in the water, at the same time, the major portion of the oxidant dissolves more rapidly than the major portion of the reductant. The lenses can be worn immediately after treatment without the need for water washing.

CA patent application nr. 2,044,072 (Webb), WO 93/17720 (Webb) and EP patent application nr. 196,151 (Hopkinson) disclose chloramine-T used for disinfecting contact lenses. No use of proteases is mentioned in these patent documents.

U.S. Pat. No. 5,057,414 (Stief et al.) concerns determining activity of serine proteases and inhibitors in plasma, including treatment with e.g. chloramine-T or chloramine-B as an oxidizing agent and a detergent to inactivate specific inhibitors. The patent does not concern cleaning or disinfecting of contact lenses.

EP patent application nr. 147,100 (Ciba Geigy) concerns cleaning and disinfecting of contact lenses with a hydrogen peroxide solution in the presences of a solid sustained release composition which slowly releases a peroxide inactivator. The lenses may be treated with a wetting or comfort solution before inserting into the eyes. However, cleaning and disinfection with hydrogen peroxide does not remove proteinaceous deposits effectively from the surface of the contact lenses.

EP patent application nr. 279.401 (Dr. Thilo & Co. Gmbh) discloses a disinfection and cleaning product for contact lenses containing a chlorine releasing compound, at least one protease and conventional formulation assistants. Initially the chlorine releasing compound, which must be characterized as a strong disinfecting agent, is added to the solution. After sufficient disinfecting, the protease is added to clean the lenses by degrading protein deposits on the lenses surface. The remaining chlorine releasing compound is inactivated by the protease. After the disinfecting and cleaning process the contact lenses must be rinsed thoroughly to remove active protease to avoid damage of the eyes.

A drawback of the techniques disclosed in the prior art documents is that the cleaning and disinfecting of contact lenses with enzymes must be succeeded by a thorough rinsing procedure to secure removal of all remaining enzyme activity before inserting the contact lenses into the eyes. This makes the procedures cumbersome and implies a risk of forgetting the rinsing step, which may lead to exposing the eyes to enzymatic activity and/or disinfecting agents, which will irritate or even might damage the eyes.

SUMMARY OF THE INVENTION

It is the object of the invention to provide a facilitated and secure method for simultaneous cleaning, disinfecting and preserving contact lenses, which allows the contact lens wearer to insert the contact lenses after cleaning and disinfection, without additional rinsing or washing or followed by only sparingly rinsing.

The above mentioned problems are overcome by a method for simultaneous cleaning, disinfecting and preserving contact lenses comprising treating contact lenses in the following order with:

1) at least one enzyme,
2) at least one enzyme inhibitor,
3) at least one mild disinfecting agent, and
4) optionally rinsing in e.g. a physiological saline solution.

According to a preferred embodiment of the invention the enzyme inhibitor is a carbonyl hydrolase inhibitor, which is also a mild disinfecting agent.

In a specific embodiment of the invention the enzyme inhibitor is chloramine-T or chloramine-B.

A second object of the invention is to provide a contact lens cleaning, disinfecting and preserving product, comprising at least one enzyme, at least one enzyme inhibitor and at least one mild disinfecting agent.

Another object of the invention is to provide a tablet or capsule for cleaning, disinfecting and preserving contact lenses comprising at least one enzyme inhibitor.

In an embodiment of the tablet or capsule of the invention said enzyme inhibitor is released slowly or delayed to the aqueous solution.

Still another object of the invention is to provide for the use of an enzyme inhibitor for cleaning, disinfecting and preserving contact lenses.

In a specific embodiment of the invention chloramine-T or chloramine-B is used as said enzyme inhibitor.

DETAILED DESCRIPTION OF THE INVENTION

The present invention can be used with all groups of contact lenses including hard, soft, rigid gas permeable lenses and silicone lenses. Nevertheless, the invention is preferably employed with cleaning and disinfecting soft hydrogel lenses which absorb significant amounts of water.

Hydrogel lenses are commonly prepared from monomers or polymers, such as N,N-dimethyl acylamide, 2-hydroxyethyl methacrylate, hydroxyethylmethyl methacrylate, N-vinyl pyrrolidone, poly vinyl pyrrolidone, vinyl acetate, glyceryl methacrylate, flour silicon methacrylate, butyl methacrylate, isobutyl methacrylate, 3-methoxy-2-hydroxypropyl methacrylate, pentyl methacrylate, cyclohexyl methacrylate, alkyl methacrylate, glycerol methacrylate, methyl methacrylic acid, methacrylic acid or methacrylic acid ester, and the like.

The object of the invention is to provide a facilitated and secure method for simultaneously cleaning, disinfecting and preserving contact lenses comprising treating contact lenses in the following order with:

1) at least one enzyme,
2) at least one enzyme inhibitor,
3) at least one disinfecting agent, and
4) optionally rinsing in e.g. physiological saline solution.

According to the present invention the enzyme used as a cleaning agent is added before the mild disinfection agent and/or the enzyme inhibitor. This will secure that the eyes will not be damaged even if the rinsing procedure is not used or forgotten.

The optional rinsing step is performed to make sure that the remaining disinfecting agent is removed from the lenses. It is to be understood that the step may be superflous and may be left out, due to the use of a mild disinfecting agent which is acceptable for the eyes.

In this case it is possible to use only one solution to clean, disinfect and store contact lenses, which makes the method less cumbersome in comparison to prior art methods.

If the enzyme inhibitory effect is reversible the optional rinsing step is mandatory. This is due to the risk that the inhibitory effect of the enzyme inhibitor ceases to exist, e.g. when diluted in an aqueous solution or tear solution, change of the physical conditions, such as pH and ionic strength, the presence of other components etc.

However, it is to be understood that this does not imply that it is mandatory that the enzyme inhibitor is an irreversible enzyme inhibitor, but it is required that the enzyme inhibitor inhibit enzyme activity to such an extend that the eyes are not damaged during wear of the contact lenses.

In an embodiment of the invention said contact lenses are first immersed in an aqueous solution, secondly treated with at least enzyme, for a period of time sufficient to degrade deposits on the contact lenses' surface, then treated with at least one enzyme inhibitor for a period of time sufficient to inhibit remaining enzyme, and finally disinfected.

The enzymes used for the cleaning of contact lenses according to the invention are carbonyl hydrolases, which exhibits proteolytic, lipolytic, amylolytic or related activities.

The enzymes may be neutral, acidic or alkaline. However, it is preferred that the enzymes have substantial activity at pH between 6.0 and 8.5.

Preferred enzymes used for the cleaning process are proteases selected from the group comprising serine proteases, acidic aspartic proteases, cysteine proteases and metallo proteases, respectively. As suitable enzymes are also contemplated truncated, modified enzymes or variants of the above listed groups.

Examples of preferred serine proteases are e.g. trypsins, chymotrypsins and subtilisins.

Most preferred are the Bacillus derived alkaline serine proteases, such as subtilisin BPN', subtilisin Carlsberg, subtilisin PB92, subtilisin 309, subtilisin 147, subtilisin 168, subtilisin DY, aqualysin or thermitase, truncations, modification and variants thereof.

Specific examples of cysteine proteases are e.g. papain and bromelain.

To the group of suitable metallo proteases are e.g. Neutrase® and collagenase.

Specific examples of acidic aspartic proteases are e.g. pepsin A, pepsin B, pepsin C, chymosin, cathepsin B and renin.

In an embodiment of the invention the enzyme inhibitor is a carbonyl hydrolase inhibitor. Also contemplated are reversible enzyme inhibitors acting as irreversible enzyme inhibitors under the conditions present in the eyes.

Examples of metallo protease inhibitors are EDTA and metal chelating agents.

Specific examples of compounds that inhibit serine proteases are chloramine-T and chloramine-B.

In a preferred embodiment of the invention said enzyme inhibitor exhibits a mild disinfecting effect on the contact lenses.

Chloramine-T and chloramine-B are specific examples of compounds exhibiting enzyme inhibitory effect as well as disinfecting effect.

Other examples of combined enzyme inhibitors/disinfectants are bacitracin and aryl boronic acids.

According to the invention the enzyme is present in a concentration sufficient for degrading deposits on the surface of the contact lenses and the enzyme inhibitor is present in a concentration sufficient to inhibit all remaining enzyme activity.

The specific amounts of enzyme and enzyme inhibitor are easily determined by one skilled in the art and are dependent upon the time allowed for removing the deposits, the activity of the enzyme and enzyme inhibitor, the purity of the enzyme etc.

In a specific embodiment of the invention chloramine-T is used as the enzyme inhibitor and the disinfecting agent. Chloramine-T is present in a concentration of 0.0001% to 5%, preferably of 0.001% to 1%.

Another object of the invention is to provide a contact lens cleaning, disinfecting and preserving product, comprising at least an enzyme and at least an enzyme inhibitor.

In an embodiment of the invention the product comprises an aqueous solution and a tablet. Said solution preferably comprises an enzyme and said tablet comprises an enzyme inhibitor.

In another embodiment of the invention the contact lens product comprises at least two tablets, one of which comprises said enzyme and the other comprises said enzyme inhibitor.

Preferably the product comprises a multi layer tablet, wherein an outer layer or coating comprises said enzyme(s) and an inner layer or core comprises said disinfecting agent and enzyme inhibitor. Said core and outer layer may be separated by a barrier or a membrane.

Said barrier may in an embodiment of the invention be made of a water soluble polymer layer, preferably a water soluble film.

Examples of said water soluble film comprises polymers soluble in an acidic medium, such as polymers of dimethylaminomethacrylate and neutral methacrylate esters.

Alternatively the film comprises a pH neutral soluble polymer. Suitable polymers are e.g. soluble cellulose ethers, such as methylcellulose, methylhydroxycellulose, methylhydroxyethylcellulose, hydroxypropylcellulose, hydroxyethylcellulose, sodium carboxymethylcellulose, cellulose acetate phthalate, hydroxypropylmethylcellulose phthalate, a polymer of methacrylic acid and methacrylate esters, a copolymer of methacrylic acid and methacrylate esters, a copolymer of methyl vinyl ether and maleic acid anhydride and polyvinyl alcohols.

In still another embodiment the contact lens product comprises a tablet comprising a sparingly soluble matrix comprising the enzyme(s) wherein the enzyme inhibitor is dispersed or distributed.

In a preferred embodiment the tablet is a controlled release tablet.

Suitable plasticizers of polyhydric alcohols and water may be added to the above listed soluble film polymers to control the diffusion rate. Preferred plasticizers for this purpose are 1,2-propylene glycol, polyethylene glycols and citrate esters.

In a specific example the enzyme inhibitor is chloramine-T or chloramine-B, preferably present in a concentration of 0.0001% to 5%, preferably 0.001% to 1%.

Considered as suitable enzyme inhibitors are also peptide aldehydes, peptide ketones, such as peptide chloromethyl ketones, and cyclic peptides, such as bacitracin, and aryl boronic acids.

Suitable enzymes which may be used according to the invention are mentioned above.

Still another object of the invention is to provide a tablet or capsule for cleaning, disinfecting and preserving contact lenses, comprising an enzyme inhibitor, which may further comprise an enzyme.

In a specific embodiment of the invention the tablet or capsule comprises chloramine-T or chloramine-B as the enzyme inhibitor.

In a preferred embodiment the tablet or capsule is of the controlled release type, wherein said enzyme is first released and said enzyme inhibitor is released after a time sufficient for the said enzyme to degrade composites on the contact lenses.

In an alternative embodiment said enzyme inhibitor is released slowly or delayed to the aqueous solution.

A final object of the invention is to provide for the use of an enzyme inhibitor in the cleaning, disinfecting and preserving of contact lenses. The enzyme inhibitor may be selected from the group of compounds mentioned above, such as a carbonyl hydrolases.

In a specific embodiment the enzyme inhibitor is chloramine-T or chloramine-B.

According to the invention the disinfecting agent used must be a mild disinfecting agent.

Additional components may be added to or incorporated into the tablets or capsules which do not substantially decrease the activity of the active components.

Examples are components such as effervescing agents, stabilizers, buffers, chelating agent and/or sequestering agents, colouring agent, tonicity adjusting agents, surfactant and the like. In addition binders, lubricants, carriers, and other excipients normally used in producing tablets may be incorporated.

Examples of suitable buffering agent include alkali metal salts, such as potassium or sodium carbonates, acetates, borates phosphates, citrates, and hydroxides, and weak acids such as acetic and boric acids.

Effervescing agents are typically employed when the enzyme is provided i solid form. Examples of suitable effervescing agent include, tartaric or citric acid used in combination with suitable alkali metal salts, such as sodium carbonate.

In the case of the cleaning, disinfecting and preserving product comprising an aqueous solution, it may contain one or more of suitable buffering agents (as listed above), chelating agents and/or sequestering agent, tonicity adjusting agent and surfactant.

Suitable tonicity adjusting agents include sodium and potassium chloride, dextrose, calcium and magnesium chloride.

Suitable surfactants can either be cationic, anionic, nonionic or amphoteric. Preferred surfactants are neutral or nonionic.

Specific examples include polyethylene glycol ethers of fatty acids, polyoxypropylene ethers of C12–C18 alkanes and polyxyethylene, polyoxypropylene block copolymers of ethylene diamine (i.e. poloxamine).

Examples of preferred chelating agents include Ethylenediaminetetraacetic acid (EDTA) and its salts (disodium) and certain polyvinyl alcohols.

MATERIALS AND METHODS

Enzymes
Savinase®: Alcalophilic subtilisin from Bacillus lentus
Subtilisin A®: Subtilisin Carlsberg type
Esperase®: Alcalophilic subtilisin from Bacillus lentus
All enzymes are available from Novo Nordisk A/S.
Chloramine-T
Chloramine T (Trihydrate) p.a. Merck art 2426
Mw=281.69 g/mol, 1% equals approx. 36 mM
Protease Activity Analysis with Suc-Ala-Ala-Pro-Phe-pNA The substrate (succinyl-Alanine-Alanine-Proline-Phenylalanine-para-nitroanilide. Sigma no. S-7388, Mw 624.6 g/mole.

Proteases especially chymotrypsin cleaves the bond between the peptide and p-nitroaniline to give a visible yellow colour absorbing at 405 nm.

Buffer: e.g. Britton and Robinson buffer pH 8.3
Substrate: 100 mg suc-AAPF-pNA is dissolved into 1 ml dimethyl sulfoxide (DMSO). 100 μl of this is diluted into 10 ml with Britton and Robinson buffer.

Analysis: Substrate and protease solution is mixed and the absorbance is monitored at 405 nm as a function of time and $ABS_{405\ nm}$/min. The temperature should be controlled (20–50° C. depending on protease). This is a measure of the protease activity in the sample.

Contact Lenses
Revolution, Sunsoft, type 4
Buffer
0.05 M K-phosphate Britton and Robinson buffer pH 8.3
Solutions Solution A: 1 mg/ml solution of suc-Alanine-Alanine-Proline-Phenylalanine-para-nitroanilide (s-AAPF-pNA)
Substrate: 100 mg suc-AAPF-pNA is dissolved into 1 ml dimethyl sulfoxide (DMSO). 100 μl of this is diluted into 10 ml with Britton and Robinson buffer.

Procedures
Test for the Inhibitory Effect of Chloramine-T

The enzyme is incubated for 5 minutes, 1 hour, 4 hours and 27 hours in MilliQ-water and 0.90% NaCl aqueous solution as incubation solutions with and without chloramine-T. Then protease activity analysis are performed, using the suc-AAPF-pNA method, and using a non-incubated enzyme solution as a blind.

The incubation solutions are diluted to $3*10^{-4}$ and $3*10^{-5}$ KNPU(S)/ml.

Test for Protease Activity on Contact Lenses

A contact lens (sunsoft) is soaked in 1.5 ml of the protease solution for 20 hours at room temperature.

The lens is rinsed in buffer and divided into two. One half lens is then soaked for 1 hour in 1% chloramine-T in buffer, the other half lens is soaked in buffer.

Thereafter the residual protease activity on the lens is measured by applying 7.5 μl of solution A and incubated in a sealed container for 20 minutes.

Protease activity will cause solution A to hydrolyse and produce a yellow colour on the surface of the lenses.

EXAMPLES

Experiments
The following experiments were preformed as described in the section "METHODS AND MATERIALS".

All enzymes and solutions used are described in the section "METHODS AND MATERIALS".

Example 1

Experiment A
The inhibitory effect of chloramine-T was tested on Savinase® in MilliQ-water (table 1) and 0.9% NaCl aqueous solution (table 2):

In table 1 and table 2 the results of the analysis are displayed.

TABLE 1

| | 1% Chloramine-T | | 0.01% Chloramine-T | | 0.01% Chloramine-T | |
|---|---|---|---|---|---|---|
| | $3*10^{-5}$ KNPU per ml | $3*10^{-4}$ KNPU per ml | $3*10^{-5}$ KNPU per ml | $3*10^{-4}$ KNPU per ml | $3*10^{-5}$ KNPU per ml | $3*10^{-4}$ KNPU per ml |
| 5 min | 0 | 0 | 0 | 0 | 0 | 6 |
| 1 h | 0 | 0 | 0 | 0 | 0 | 2 |
| 4 h | 0 | 0 | 0 | 0 | 0 | 0 |
| 27 h | 0 | 0 | 0 | 0 | 0 | 0 |

The inhibitory effect of chloramine-T on Savinase ® in MilliQ-water as % remained enzyme activity.

TABLE 2

| | 1% Chloramine-T | | 0.1% Chloramine-T | | 0.01% Chloramine-T | |
|---|---|---|---|---|---|---|
| | $3*10^{-5}$ KNPU per ml | $3*10^{-4}$ KNPU per ml | $3*10^{-5}$ KNPU per ml | $3*10^{-4}$ KNPU per ml | $3*10^{-5}$ KNPU per ml | $3*10^{-4}$ KNPU per ml |
| 5 min | 0 | 0 | 2 | 3 | 5 | 6 |
| 1 h | 3 | 0 | 3 | 0 | 6 | 5 |
| 4 h | 2 | 0 | 0 | 0 | 3 | 2 |
| 27 h | 0 | 0 | 0 | 0 | 0 | 0 |

The inhibitory effect of chloramine-T on Savinase ® in 0.9% NaCl aqueous solution as % remained enzyme activity.

Experiment B

The inhibitory effect of chloramine-T was tested on subtilisin A in MilliQ-water (table 3) and in a 0.9% NaCl aqueous solution (table 4):

In table 3 and table 4 the results of the analysis are displayed.

TABLE 3

| | 1% Chloramine-T | | 0.1% Chloramine-T | | 0.01% Chloramine-T | |
|---|---|---|---|---|---|---|
| | $3*10^{-5}$ KNPU per ml | $3*10^{-4}$ KNPU per ml | $3*10^{-5}$ KNPU per ml | $3*10^{-4}$ KNPU per ml | $3*10^{-5}$ KNPU per ml | $3*10^{-4}$ KNPU per ml |
| 5 min | 0 | 0 | 0 | 0 | 4 | 6 |
| 1 h | 0 | 0 | 2 | 0 | 3 | 0 |
| 4 h | 0 | 0 | 0 | 0 | 0 | 0 |
| 27 h | 0 | 0 | 0 | 0 | 0 | 0 |

The inhibitory effect of chloramine-T on subtilisin A in MilliQ-water as % remained enzyme activity.

TABLE 4

| | 1% Chloramine-T | | 0.1% Chloramine-T | | Chloramine-T | |
|---|---|---|---|---|---|---|
| | $3*10^{-5}$ KNPU per ml | $3*10^{-4}$ KNPU per ml | $3*10^{-5}$ KNPU per ml | $3*10^{-4}$ KNPU per ml | $3*10^{-5}$ KNPU per ml | $3*10^{-4}$ KNPU per ml |
| 5 min | 0 | 0 | 0 | 0 | 2 | 4 |
| 1 h | 0 | 0 | 2 | 0 | 3 | 0 |
| 4 h | 0 | 0 | 0 | 0 | 2 | 0 |
| 27 h | 0 | 0 | 0 | 0 | 0 | 0 |

The inhibitory effect of chloramine-T on subtilisin A in 0.9% Nail aqueous solution as % remained enzyme activity.

Experiment C

The inhibitory effect of chloramine-T was tested on Esperase® in MilliQ-water (table 5) and in a 0.9% NaIl aqueous solution (table 6):

In table 5 and table 6 the results of the analysis are displayed.

TABLE 5

| | 1% Chloramine-T | | 0.1% Chloramine-T | | 0.01% Chloramine-T | |
|---|---|---|---|---|---|---|
| | $3*10^{-5}$ KNPU per ml | $3*10^{-4}$ KNPU per ml | $3*10^{-5}$ KNPU per ml | $3*10^{-4}$ KNPU per ml | $3*10^{-5}$ KNPU per ml | $3*10^{-4}$ KNPU per ml |
| 5 min | 0 | 0 | 0 | 0 | 8 | 9 |
| 1 h | 0 | 0 | 0 | 0 | 5 | 3 |
| 4 h | 0 | 0 | 0 | 0 | 0 | 2 |
| 27 h | 0 | 0 | 0 | 0 | 0 | 0 |

The inhibitory effect of chloramine-T on Esperase ® in MilliQ-water as % remained enzyme activity.

TABLE 6

| | 1% Chloramine-T | | 0.1% Chloramine-T | | 0.01% Chloramine-T | |
|---|---|---|---|---|---|---|
| | $3*10^{-5}$ KNPU per ml | $3*10^{-4}$ KNPU per ml | $3*10^{-5}$ KNPU per ml | $3*10^{-4}$ KNPU per ml | $3*10^{-5}$ KNPU per ml | $3*10^{-4}$ KNPU per ml |
| 5 min | 0 | 0 | 6 | 5 | 16 | 16 |
| 1 h | 0 | 0 | 0 | 0 | 11 | 7 |
| 4 h | 0 | 0 | 0 | 0 | 4 | 5 |
| 27 h | 0 | 0 | 0 | 0 | 0 | 3 |

The inhibitory effect of chloramine-T on Esperase ® in 0.9% NaIl aqueous solution as % remained enzyme activity.

Example 2

Test of the Protease Activity on Contact Lenses

Solutions of 0,01 KNPU Savinase/ml, 0.01 M KNPU Esperase®/ml, and 0,002 subtilisin A AU/ml, respectively, all in K-phosphate buffer, were tested for protease activity, as described above under "Methods and Materials".

All lenses soaked in buffer showed the presence of active protease on the lens after rinsing.

All lenses soaked with chloramine-T showed no protease activity. This result indicated that even adsorbed protease can be inhibited by adding an enzyme inhibitor.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A contact lens cleaning and disinfecting product, comprising (i) an aqueous solution comprising at least one protease, wherein said protease is present at a concentration sufficient for degrading deposits on the surface of contact lenses; and (ii) a tablet comprising at least one inhibitor of said protease selected from the group consisting of chloramine-T and chloramine-B, wherein said inhibitor is present at a concentration which, when said tablet is dissolved in said solution, is sufficient to inhibit remaining protease activity of said protease and to disinfect said contact lens.

2. The contact lens cleaning and disinfecting product according to claim 1, wherein said tablet further comprises a plasticizer selected from the group consisting of polyhydric alcohols, polyethylene glycols, and citrate esters.

3. The contact lens cleaning and disinfecting product according to claim 1, wherein said protease is selected from the group consisting of an acidic aspartic protease, a cysteine protease, a serine protease, and a metalloprotease.

4. The contact lens cleaning and disinfecting product according to claim 3, wherein said acidic aspartic protease is selected from the group consisting of pepsin A, B or C, and cathepsin D; said cysteine protease is papain; and said serine protease is a subtilisin.

5. A contact lens cleaning and disinfecting product comprising a multi layer tablet, wherein said tablet comprises (i) an outer layer comprising at least one protease in sufficient concentration to degrade deposits on the surface of a contact lens and (ii) an inner layer comprising at least one inhibitor of said protease selected from the group consisting of chloramine-T and chloramine-B in sufficient concentration to inhibit remaining protease activity and to disinfect said contact lens.

6. The contact lens cleaning and disinfecting product according to claim 5, wherein said inner and outer layers are separated by a barrier.

7. The contact lens cleaning and disinfecting product according to claim 6, wherein said barrier is a water soluble polymer layer.

8. The contact lens cleaning and disinfecting product according to claim 7, wherein said soluble polymer layer comprises compounds selected from the group consisting of polymers of dimethylaminomethacrylate; soluble cellulose ethers; polymers of methacrylic acid; polymers of methacrylate esters; copolymers of methacrylic acid and methacrylate esters; copolymers of methyl vinyl ether and maleic acid anhydride; and polymers of polyvinyl alcohols.

9. The contact lens cleaning and disinfecting product according to claim 8, wherein said soluble cellulose esters are selected from the group consisting of methylcellulose, methylhydroxycellulose, methylhydroxyethylcellulose, hydroxypropylcellulose, hydroxyethylcellulose, sodium carboxymethyl cellulose, cellulose acetate phthalate, and hydroxypropylmethylcellulose phthalate.

10. The contact lens cleaning and disinfecting product according to claim 5, wherein said protease is selected from the group consisting of an acidic aspartic protease, a cysteine protease, a serine protease and a metalloprotease.

11. The contact lens cleaning and disinfecting product according to claim 10, wherein said aspartic protease is selected from the group consisting of pepsin A, B or C, and cathepsin D; said cysteine protease is papain; and said protease is a subtilisin.

12. A contact lens cleaning and disinfecting product comprising a multi layer tablet, wherein said tablet comprises (i) an outer layer comprising subtilisin A in sufficient concentration to degrade deposits on the surface of the contact lens and (ii) an inner layer comprising chloramine-T in sufficient concentration to inhibit remaining protease activity and to disinfect said contact lens.

13. A method of cleaning and disinfecting contact lenses comprising treating contact lenses sequentially with:
   1) at least one protease in sufficient concentration to degrade deposits on the surface of the contact lens, and
   2) at least one inhibitor of said protease selected from the group consisting of chloramine-T and chloramine-B in sufficient concentration to inhibit remaining activity of said protease and to disinfect said contact lens.

14. The method according to the claim 13, wherein said protease is selected from the group consisting of an acidic aspartic protease, a cysteine protease, a serine protease and a metallo protease.

15. The method according to claim 14, wherein said acidic aspartic protease is selected from the group consisting of pepsin A, B or C, and cathepsin D.

16. The method according to claim 14, wherein said cysteine protease is papain.

17. The method according to claim 14, wherein said serine protease is a subtilisin.

18. A method according to claim 13, further comprising rinsing said treated contact lenses.

19. A method of cleaning and disinfecting contact lenses, which comprises:
1) immersing said lenses in an aqueous solution,
2) treating said immersed lenses with a protease in sufficient concentration and for a period of time sufficient to degrade deposits on the contact lenses' surface, and
3) treating said lenses with an inhibitor of said protease selected from the group consisting of chloramine-T and chloramine-B in sufficient concentration and for a period of time sufficient to inhibit remaining protease activity and to disinfect said contact lens.

20. The method according to claim 19, wherein said protease is selected from the group consisting of an acidic aspartic protease, a cysteine protease, a serine protease and a metalloprotease.

21. A method of cleaning and disinfecting contact lenses comprising treating contact lenses sequentially with:
1) subtilisin A in sufficient concentration to degrade deposits on the surface of the contact lens and
2) chloramine-T in sufficient concentration to inhibit remaining protease activity and to disinfect said contact lens.

* * * * *